| United States Patent [19] | [11] | 4,316,955 |
|---|---|---|
| Abbott et al. | [45] | Feb. 23, 1982 |

[54] ENZYMATIC DEESTERIFICATION OF CEPHALOSPORIN METHYL ESTERS

[75] Inventors: Bernard J. Abbott; Dennis R. Berry, both of Greenwood, Ind.

[73] Assignee: Eli Lilly and Company, Indianapolis, Ind.

[21] Appl. No.: 205,538

[22] Filed: Nov. 10, 1980

[51] Int. Cl.³ .......................... C12P 35/00; C12N 9/18
[52] U.S. Cl. ....................................... 435/47; 435/197; 435/253; 435/886
[58] Field of Search .................. 435/47, 197, 886, 253

[56] References Cited

U.S. PATENT DOCUMENTS 3,749,641 7/1973 Takahashi et al. .................... 435/51
3,761,356 9/1973 Daniels ................................ 435/197

OTHER PUBLICATIONS

Abbott et al., Applied Microbiology, vol. 30, No. 3 pp. 413–419 (Sep. 1975).
Brannon et al., The Journal of Antibiotics, vol. 24, No. 2 pp. 121–124 (Feb. 1976).

*Primary Examiner*—Lionel M. Shapiro
*Attorney, Agent, or Firm*—Joseph A. Jones; Arthur R. Whale

[57] ABSTRACT

The microorganism *Streptomyces capillispira*, NRRL 12279, produces an enzyme which deesterifies cephalosporin methyl esters.

20 Claims, No Drawings

ENZYMATIC DEESTERIFICATION OF CEPHALOSPORIN METHYL ESTERS

BACKGROUND

This invention belongs to the field of enzyme chemistry and the synthesis of antibiotics, and provides a method of deesterifying cephalosporin methyl esters by contact with an enzyme derived from fermentation.

STATE OF THE ART

Many enzymes have been found to be useful for synthesizing or degrading organic compounds. For example, U.S. Pat. No. 3,749,641, of Takeda Chemical Industries, teaches that enzymes derived from any of a great number of microorganisms are capable of deesterifying and deacylating cephalosporin compounds. U.S. Pat. No. 3,761,356, of the Upjohn Co., discloses an enzyme, derived from a marine animal, which will deesterify prostaglandin-like compounds, and the literature on esterases in general has been surveyed by Myers and Hofstee, in chapters 28 and 29 of The Enzymes, Boyer, Lardy and Myrback, Eds., Vol. 4 (Academic Press 1960).

SUMMARY OF THE INVENTION

This invention provides a novel enzyme which is produced by *Streptomyces capillispira* when cultured under enzyme-producing conditions, which enzyme deesterifies cephalosporin methyl esters of the formula

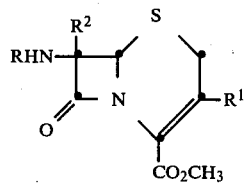

wherein

R is hydrogen or $R^3CH(NH_2)CO-$; $R^1$ is methyl, chloro, acetoxymethyl, methoxy, methoxymethyl, aminocarbonyloxymethyl, methylthiadiazolylthiomethyl or methyltetrazolylthiomethyl;

$R^2$ is hydrogen or methoxy;

$R^3$ is phenyl, cyclohexadienyl, cyclohexadienyl monosubstituted with hydroxy, or phenyl mono- or disubstituted with halo, hydroxy, $C_1$–$C_3$ alkyl or $C_1$–$C_3$ alkoxy; to form the corresponding carboxylic acid.

The invention also provides a process for deesterifying cephalosporin methyl esters of the above formula, comprising contacting the methyl ester with the enzyme produced by culturing *Streptomyces capillispira* under enzyme-producing conditions.

DESCRIPTION OF THE PREFERRED EMBODIMENTS

In this document, all temperatures are expressed in degrees Celsius.

The general chemical terms above have their usual meanings in organic chemistry. The term "halo" refers to fluoro, chloro, bromo or iodo. The terms "$C_1$–$C_3$ alkyl" and "$C_1$–$C_3$ alkoxy" refer to groups such as methyl, methoxy, ethyl, ethoxy, propyl, isopropoxy, and the like.

The above general formula describing the substrate compounds which are deesterified by the process of this invention is believed to be entirely clear. A group of representative compounds will be presented, however, to assure that the reader understands the compounds acted upon by the enzyme of this invention.

methyl 7-amino-3-acetoxymethyl-3-cephem-4-carboxylate methyl 7-amino(2-chlorophenyl)acetamido-3-chloro-7-methoxy-3-cephem-4-carboxylate methyl 7-amino(2,6-dichlorophenyl)acetamido-3-methyl-3-cephem-4-carboxylate methyl 7-amino(2,5-cyclohexadienyl)acetamido-3,7-di(-methoxy)-3-cephem-4-carboxylate methyl 7-amino(phenyl)acetamido-3-methoxymethyl-3-cephem-4-carboxylate methyl 7-amino(4-bromophenyl)acetamido-3-aminocarbonyloxymethyl-7-methoxy-3-cephem-4-carboxylate methyl 7-amino(3-fluorophenyl)acetamido-3-(5-methyl-1,3,4-thiadiazol-2-ylthiomethyl)-3-cephem-4-carboxylate methyl 7-amino(3-iodophenyl)acetamido-7-methoxy-3-(1-methyltetrazol-5-ylthiomethyl)-3-cephem-4-carboxylate methyl 3-acetoxymethyl-7-amino(2-chloro-4-fluorophenyl)acetamido-3-cephem-4-carboxylate methyl 7-amino(4-methylphenyl)acetamido-3-chloro-3-cephem-4-carboxylate methyl 7-amino(3-propylphenyl)acetamido-7-methoxy-3-methyl-3-cephem-4-carboxylate methyl 7-amino(3,5-dimethylphenyl)acetamido-3-chloro-3-cephem-4-carboxylate methyl 7-amino(5-bromo-2-methylphenyl)acetamido-3-chloro-7-methoxy-3-cephem-4-carboxylate methyl 7-amino(4-iodo-3-isopropylphenyl)acetamido-3-aminocarbonyloxymethyl-3-cephem-4-carboxylate methyl 7-amino(4-ethoxyphenyl)acetamido-3-chloro-3-cephem-4-carboxylate methyl 7-amino[2,4-di(propoxy)phenyl]acetamido-3-methyl-3-cephem-4-carboxylate methyl 3-acetoxymethyl-7-amino(3-bromo-5-methoxyphenyl)acetamido-7-methoxy-3-cephem-4-carboxylate methyl 7-amino(2-ethyl-6-propoxyphenyl)-acetamido-3-methoxymethyl-3-cephem-4-carboxylate methyl 7-amino(4-hydroxy-2,5-cyclohexadienyl)-acetamido-3-chloro-3-cephem-4-carboxylate methyl 7-amino(2-hydroxy-2,4-cyclohexadienyl)-acetamido-3-(5-methyl-1,3,4-thiadiazol-2-ylthiomethyl)-7-methoxy-3-cephem-4-carboxylate methyl 7-amino(4-hydroxyphenyl)acetamido-3-chloro-3-cephem-4-carboxylate methyl 7-amino(2,5-dihydroxyphenyl)acetamido-3-methoxy-3-cephem-4-carboxylate methyl 3-acetoxymethyl-7-amino(3-chloro-4-hydroxyphenyl)acetamido-7-methoxy-3-cephem-4-carboxylate methyl 7-amino(3-ethyl-5-hydroxyphenyl)acetamido-7-methoxy-3-(5-methyltetrazol-1-ylthiomethyl)-3-cephem-4-carboxylate Certain classes of the substrate compounds used in this invention are preferred, and certain conditions of operating the deesterification process are preferred conditions. The table below lists the preferred substrates and conditions. It will be understood that the various limitations below may be combined to create other, more limited preferred modes of the invention.

A. $R^1$ is methyl;

B. $R^1$ is chloro;

C. $R^1$ is methyl or chloro;

D. $R^1$ is acetoxymethyl, methyl or chloro;
E. $R^2$ is hydrogen;
F. R is hydrogen;
G. $R^3$ is phenyl;
H. $R^3$ is phenyl, hydroxyphenyl, cyclohexadienyl, or hydroxycyclohexadienyl;
I. R is hydrogen, or $R^3$ is phenyl;
J. The enzyme is immobilized;
K. The pH is from about 7 to about 9;
L. The temperature is from about 15° to about 45°.

The preferred individual substrate compounds are methyl 7-amino(phenyl)acetamido-3-methyl-3-cephem-4-carboxylate, methyl 7-amino-3-methyl-3-cephem-4-carboxylate, methyl 7-amino-3-chloro-3-cephem-4-carboxylate and methyl 7-amino(phenyl)acetamido-3-chloro-3-cephem-4-carboxylate.

The microorganism which produces the enzyme of this invention is a new species, *Streptomyces capillispira*, which has been designated A49492. It was isolated as a substantially biologically pure culture from a sample of soil collected in Sweden, and has been deposited at the Northern Regional Research Laboratory, Agricultural Research Service, United States Department of Agriculture, Peoria, Ill., under the number NRRL 12279.

A49492 has been characterized by the methods recommended by the International Streptomyces Project (ISP) for the characterization of Streptomyces species, as described by Shirling and Gottlieb, Int. J. Syst. Bacteriol. 16, 313–40 (1966), along with certain supplementary tests.

Cell wall analyses were performed on cultures grown in yeast-malt extract broth (ISP No. 2) for 24 hours at 30°. The mycelia were collected by centrifugation and washed 3 times with distilled water. The washed cells were then lyophilized, and the cell wall sugars were determined substantially according to the method of Lechavalier, 1971, Chemical Methods as Criteria for the Separation of Actinomyces into Genera, Workshop sponsored by the subcommittee on Actinomyces of the American Society for Microbiology, T. G. Pridham, Convener, held at the Institute of Microbiology, Rutgers Univ., The State Univ. of New Jersey, New Brunswick, N.J. Diaminopimelic acid isomers were determined by the method of Becker et. al., *Appl. Microbiol.* 12, 421–423 (1964). The results are tabulated below.

The pH range for growth was measured using the following buffers at 0.05 M in ISP No. 2 agar plates: citric acid, pH 3,4,5; 2-morpholinoethanesulfonic acid, pH 6; 3-morpholinopropanesulfonic acid, pH 7; N-tris(-hydroxymethyl)methylglycine, pH 8; 2-cyclohexylaminoethanesulfonic acid, pH 8.5, 9.0, 9.5; 3-cyclohexylaminopropanesulfonic acid, pH 10, 10.5. The pH values of the agar plates were measured with a flat surface electrode before they were inoculated.

Carbon utilization was determined on ISP No. 9 basal medium to which filter-sterilized carbon sources were added to equal a final concentration of 1.0% of the carbon source. Plates were incubated at 30° and read after 14 days.

Melanoid pigment production was determined in ISP No. 1 broth (tryptone-yeast extract), ISP No. 6 agar (peptone-yeast extract and iron), ISP No. 7 agar (tyrosine) and in modified ISP No. 7 (lacking tyrosine).

Starch hydrolysis was determined by testing for the presence of starch with iodine on ISP No. 4 agar plates (inorganic salts-starch, as described by Blazevic and Ederer, Principles Of Biochemical Tests In Diagnostic Microbiology, John Wiley and Sons, New York, 1975).

Lysozyme resistance and decomposition of casein, esculin, hypoxanthine, tyrosine and xanthine were measured by the products of Berd, *Appl. Microbiol.* 25, 665–81 (1973).

Sodium chloride and sucrose tolerance were measured using ISP No. 2 agar. Antibiotic sensitivity was determined with sensitivity discs placed onto the surface of ISP No. 2 agar plates seeded with 2% vegetative inoculum.

The methods of Blazevic and Ederer, cited above, were followed for the catalase, phosphatase and urease analyses.

ISCC-NBS Centroid Color Charts, standard sample number 2106, as issued by the National Bureau of Standards, 1958, were used to assign color names.

A49492 produces well-developed, coiled aerial mycelia, and is therefore placed in the Spirales section, according to the scheme of Pridham et al., *Appl. Microbiol.* 6, 52–79 (1958). This morphology is readily observed on all media which support the formation of aerial mycelia. Oatmeal agar (ISP No. 3), ISP No. 7, tomato paste oatmeal agar, and tap water agar allow excellent observation of the spiral morphology. The spirals are simple, open, loose coils of 2 or 3 turns. The sporophores bear chains of 10 to 50 spores. The spore shape is oval to globose in scanning electron micrographs, and the spore size ranges from $0.96 \times 0.54$ to $1.19 \times 0.71$ μm. The average size is $1.05 \times 0.62$ μm. The spore surface ornamentation is hairy. Coremia were observed on ISP No. 2 agar.

The aerial mycelium is in the gray color series of Tresner and Backus, *Appl. Microbiol.* 11, 335–38 (1963); light brownish-gray is the predominant shade. A49492 produces a non-fragmenting substrate or primary mycelium which varies from yellow-brown to brownish-black, depending on the medium on which it is grown. A brown soluble pigment is occasionally produced. The culture does not produce melanoid pigments.

The physiological characteristics of A49492 are as follows. Catalase, phosphatase and urease are produced by the culture, and casein, hypoxanthine, tyrosine and xanthine are decomposed. The culture does not liquefy gelatin, hydrolyze starch, reduce nitrate, peptonize milk, resist lysozyme or decompose esculin. Acetate, D-arabinose, melibiose, raffinose, salicin and sucrose are not utilized by the culture. Growth of A49492 occurs in a temperature range from 10° to 45°, with an optimum temperature of 30°. A49492 will tolerate a pH range from 6 to 9.5, sodium chloride up to 6%, and sucrose concentration up to 35%.

Analyses of cell wall hydrolysates by paper chromatography showed the presence of diaminopimelic acid. No meso isomer was detected. Sugar determinations indicated that only glucose and ribose were present. This information indicates a type I cell wall and a type C sugar pattern, as described by Bergey's Manual of Determinative Bacteriology, Buchanan and Gibbons (Eds.), 8th Edition, page 658, The Williams and Wilkins Co., Baltimore, 1974. The morphological and chemical characteristics of A49492 permit a clear assignment of the organism to the Streptomyces genus.

The table below is a summary of the cultural characteristics of A49492.

| Medium | Growth | Reverse | Aerial Mycelium | Soluble Pigment |
| --- | --- | --- | --- | --- |
| ISP 2 | good | 77.m.yBr | poor:631. brGy | none |

-continued

| Medium | Growth | Reverse | Aerial Mycelium | Soluble Pigment |
|---|---|---|---|---|
| ISP 3 | fair | 63.1.br Gy | good:22. RGy | none |
| ISP 4 | good | 91.d.gy. Y | good:63.1. brGy | none |
| ISP 5 | abun. | 61. gyBr | abun:63.1. brGy | light-gray |
| ISP 7 | abun. | 59.d.Br | abun:10. pkGy | grayish-Br |
| Bennetts | good | 72.d.OY | none | none |
| Calcium malate | good | 62.d.gy Br | trace | brown |
| Czapek's | abun. | 47.d.gy. rBr | abun:264. 1.Gy | brown |
| Glucose asparagine | good | 95.m.01 Br | trace | none |
| TPO | abun. | 65.br Black | abun.63.1. BrGy | dark brown |
| Tap Water agar | poor | clear | poor | none |

The next table reports the ability of A49492 to use a number of common sources of carbon. A plus in the listing below indicates that the carbohydrate is used, a minus indicates that it is not, and a question mark indicates doubtful utilization.

TABLE 2

| Acetate | − | D-Maltose | + |
|---|---|---|---|
| D-Arabinose | − | D-Mannitol | + |
| L-Arabinose | + | Melibiose | − |
| Cellobiose | + | Raffinose | − |
| Citrate | + | Rhamnose | + |
| D-Fructose | + | D-Ribose | + |
| D-Galactose | + | Salicin | ? |
| D-Glucose | + | Sucrose | − |
| i-Inositol | + | D-Xylose | + |

The next table shows the sensitivity of A49492 to a number of common antibiotics, as measured by disk sensitivity tests. In the table below, a plus indicates that a zone of inhibition was formed, and a minus sign indicates that there was no inhibition zone. In the table below, the column headed "Amount" indicates the amount of the antibiotic deposited on each disk.

TABLE 3

| Antibiotic | Type | Amount | Result |
|---|---|---|---|
| Erythromycin | macrolide | 15 μg | − |
| Keflin | β-lactam | 30 μg | − |
| Lincomycin | lincosaminide | 2 μg | − |
| Nystatin | polyene | 100 U | − |
| Polymixin B | peptide | 300 U | − |
| Streptomycin | aminoglycoside | 10 μg | + |
| Tetracycline | perhydronaphthacene | 30 μg | + |
| Vancomycin | glycopeptide | 5 μg | + |

The following table summarizes the results of a number of tests and measurements made on the organism *Streptomyces capillispira*, A49492.

TABLE 4

| Temperature range | 10–45° |
|---|---|
| pH range | 6–9.5 |
| NaCl tolerance | 6% |
| Sucrose tolerance | 35% |
| Catalase | + |
| Phosphatase | + |

TABLE 4-continued

| Urease | + |
|---|---|
| Nitrate reductase | − |
| Gelatin liquefaction | − |
| Melanoid pigments | − |
| Skim milk | (partially utilized) |
| Starch hydrolysis | − |
| Lysozyme resistance | − |
| Casein decomposition | + |
| Esculin decomposition | − |
| Hypoxanthine decomposition | + |
| Tyrosine decomposition | + |
| Xanthine decomposition | + |

+ = positive reaction
− = negative reaction

A49492 produces the enzyme of this invention when it is cultured under proper enzyme-producing conditions. As is described above, the organism can utilize many carbohydrate sources, and the enzyme has been produced, as expected, by culturing the organism in any of numerous complex and defined media. The examples below list many media which have been successively used.

Carbohydrate sources including invert sugar, corn syrup, glucose, fructose, maltose, starch, and others have been successfully employed.

Useable nitrogen sources include peptones, soybean meal, amino acid mixtures and the like. The customary soluble inorganic salts may be used as sources of trace elements in the culture; such salts include those capable of yielding iron, sodium, potassium, ammonium, calcium, phosphate, chloride, carbonate and like ions.

It has been found, however, that the organism produces the enzyme best when it is grown in defined media. In particular, the identity and amount of the nitrogen source must be chosen with some care for best enzyme production. It has been found that amino acids, such as proline, serine, glycine and the like, may be used, but that ammonium ion is a somewhat more satisfactory nitrogen source. It appears that excessive nitrogen source, in whatever form, is inhibitory to production of the enzyme, and so it is advisable to add the nitrogen source slowly to the culture medium as growth proceeds, so that nitrogen source in excess of the culture's needs is never present.

The pH of the culture should be held in the range from about 6 to about 8, preferably from about 6.5 to about 7.5, and most preferably from about 6.9 to about 7.1. It has been found that the pH of the culture usually decreases as growth proceeds, and so it is advisable to make up the growth medium at the desired pH, and to add a base to the culture, preferably by means of an automatic controller to hold the pH at the desired point throughout the fermentation. A particularly advantageous procedure is to combine the pH adjustment with the addition of nitrogen source by adjusting the pH with ammonium hydroxide solution.

A49492 requires an adequate supply of air for growth. It is most convenient to aerate small-scale cultures in shaking flasks, and, in large scale, by submerged aerobic culture. The organism, of course, will also grow on agar slants and plates.

It is possible to inoculate a fermentation medium directly with a spore suspension, but it is preferable to use a vegetative inoculum. The vegetative inoculum is prepared by inoculating a small volume of culture medium with the spore form or mycelial fragments of the organism to obtain an actively growing culture. The vegetative inoculum is then used to inoculate a larger tank.

A49492 will grow well over a temperature range between about 25° and about 40°. It is preferable, however, to grow the organism at a temperature from about 30° to about 37°.

The fermentation time needed to produce the enzyme in a culture of A49492 is variable, but it has usually been found that good enzyme production occurs in from 2 to 7 days. Longer periods of growth can be used, but the yield of enzyme often has been found to decrease when unnecessarily long growth periods are used.

When the enzyme has been produced by a culture of A49492, it may be used by simply adding the substrate compound to the fermentation mixture, or it may be harvested and purified for use in the process of this invention. The examples below illustrate the effectiveness of simply adding the substrate compound to the fermentation mixture.

However, it may be more efficient to separate the enzyme from the culture medium, and use it in a partially purified form. The enzyme appears to be associated with the cells in the fermentation mixture. Accordingly, it is necessary to remove the cells from the culture broth and to harvest the enzyme from the separated cells. Disruption of the cells has been accomplished by homogenization, ultrasound treatment, lysis of the cells with enzymes such as lysozyme, and freezing followed by disruption of the frozen mass. Ultrasound treatment is the preferred method of disrupting the cells. The enzyme is isolated from the disrupted cells by suspending the cell homogenate in neutral or approximately neutral buffer, and filtering or centrifuging the suspension to remove disrupted cell fragments. The resulting enzyme solution may be used in the process of this invention, or may be further purified or concentrated for use.

The enzyme can be purified by passage of the enzyme solution through chromatography columns, which separate the various fractions of proteins in the solution. The purified enzyme may be further concentrated, if desired, by ultrafiltration.

The enzyme decomposes rapidly at elevated temperatures, and so it is advisable to store it at relatively low temperatures, such as 0°.

The analysis of reaction mixtures wherein the process of this invention is taking place has been easily followed by bioautography, of paper or thin-layer chromatograms, taking advantage of the fact that substrate esters are relatively inactive as antibiotics, compared to the cephalosporin acids which are the products of the present process. For example, the reaction mixture can be spotted on a thin layer chromatography plate or on filter paper, the chromatogram developed with an appropriate solvent and transferred to a nutrient agar plate inoculated with a suitable microorganism. The amount of cephalosporin acid on the chromatogram may then be estimated by comparison of the size of the zone of inhibition to zones produced by known amounts of the same cephalosporin acid on the chromatogram. When the substrate compound is a cephalosporin nucleus (wherein R is hydrogen), the product acid must be acylated before analysis, as one skilled in cephalosporin technology will understand.

Such analytical methods are used to monitor the activity of enzyme solutions as they are being harvested, purified and concentrated.

The enzyme is used in the process of this invention by simple contact of the substrate compound with the enzyme. It is preferred and customary in enzyme technology to carry out the reaction in aqueous medium. Since the enzyme has not been isolated in pure form, it is not possible to describe the absolute amount of enzyme necessary to deesterify a certain amount of substrate compound. The examples below show the method by which the activity of enzyme solutions has been measured. The operator can measure the activity of the enzyme under standard assay conditions and calculate easily from the activity the amount of the solution necessary to deesterify a given amount of substrate in a given period of time.

To make multiple re-use of the enzyme and to increase its stability, it is preferable to immobilize the enzyme by a suitable method. The immobilization of enzymes for such processes is known in the art, and the usual expedients have been found to be effective with the enzyme produced by A49492. The preferred immobilization method is ionic binding to diethylaminoethyl cellulose, which is widely sold under the trademark DEAE Sephacel, Pharmacia Fine Chemicals Corp., Piscataway, New Jersey. Another preferred immobilization method is ionic binding to DEAE cellulose in the form of beads prepared by the process of U.S. Pat. No. 4,063,017, of Tsao and Chen.

The immobilized enzyme is efficiently contacted with the substrate compound by either column or stirred-tank procedures. If a column is to be used, it is packed with the immobilized enzyme, and an aqueous solution or suspension of the substrate compound is passed through the column. When a stirred tank is used, it may be operated either continuously or batchwise according to the usual manner in the art.

After the substrate compound has been in contact with the enzyme, whether immobilized or not, for an adequate period of time to produce the desired yield of cephalosporin acid, the acid is isolated by the common organic chemical procedures. For example, it may be converted to an appropriate salt, especially a sodium or potassium salt for therapeutic use, and isolated by evaporating the water from the product solution under vacuum at moderate temperatures.

It has been found that the deesterification process may be carried out at pH's from about 7 to about 9, most preferably at a pH from about 7.5 to about 8.5. The optimum temperature for the process is from about 25° to about 30°, although temperatures from about 15° to about 45° may be used. As mentioned above, the enzyme is not particularly stable at elevated temperatures, and so it is advisable to use the optimum temperature described here. The $K_m$ value for the enzyme is about 2.3 mg./ml. for methyl 7-amino-3-methyl-3-cephem-4-carboxylate, and the concentration of the substrate compound in the reaction mixture should be in the range from about 1 to about 10 mg./ml.

It has been found that the enzyme, when in a partially purified state, can be stored for extended periods of time by freezing or lyophilization. The fermentation broth in which the enzyme is produced, and cell mass isolated from the fermentation broth, can be stored by freezing.

The following examples illustrate the production of the enzyme by fermentation of *S. capillispira*, the isolation and purification of the enzyme, and deesterification reactions carried out with the enzyme. The substrates and products of the deesterification reactions were known compounds, and so no detailed analytical identification was necessary to prove the identity of the products. Instead, the extent of deesterification was measured by an analytical method which measured the amount of acid in the reaction mixture. In some cases, the analytical method was biological, and in others, it was a titrimetric method. In addition, the production of the product was confirmed by chromatographic comparisons with authentic standards of the various cephalosporin acids.

The usual method made use of filter paper chromatography, with 4/1 acetonitrile/water as the solvent. When the chromatogram was developed, it was overlaid on an agar plate seeded with a susceptible microorganism, usually *Bacillus subtilis,* and the amount of the active antibiotic acid was measured by comparison of the size of the zone of inhibition with the zones produced by known amounts of the antibiotic on the same system.

If the substrate ester was a cephalosporin nucleus ester, having only an amino group at the 7-position, then the amount of acid could not be measured directly, because the nucleus acid is not active against the test organism. In such cases, an additional step of acylation was performed, by spraying the developed chromatogram with an acylating agent, usually a dilute solution of phenoxyacetyl chloride, to convert the inactive nucleus to an active compound.

Another detection method, called the spot plate method, was carried out by pipetting a carefully measured amount, usually 10 μl., of the mixture to be analyzed onto a filter paper sheet which had small zones outlined by lacquer so that liquids placed on the zones were isolated from each other. If the substrate compound was a nucleus ester, so that acylation was necessary, each zone was also spotted with 10 μl. of 2% sodium bicarbonate solution, and 20 μl. of 2.5% phenoxyacetyl chloride in petroleum ether. The spots were air-dried, and the paper sheets were overlaid on the agar surface of an assay plate which had been seeded with a spore suspension of *B. subtilis.* The sheets were left on the agar plates for about 45 minutes, and were then removed and the agar plates were incubated at 25° overnight. The sizes of the zones of inhibition were then measured, and the amount of cephalosporin acid in the sample was determined by comparison with the sizes of the zones produced by known amounts of the cephalosporin acid which was the product of the deesterification.

The above biological analytical methods are useful both for unpurified fermentation mixtures, and for purified enzyme preparations. Purified preparations are readily analyzed by titrimetric methods which determine the amount of acid produced by measuring the amounts of base needed to maintain constant pH during the reaction. Thus, the deesterification reaction is easily monitored with an automatic titrator by adding the enzyme preparation to an appropriate substrate solution and following the course of deesterification by the amount of base added to the sample by the automatic titrator.

The activity of the enzyme preparations in the following examples is described as a rate, usually measured in terms of (moles of substrate deesterified)/(mg. of protein or cells)(minute). In some instances, the activity of the enzyme was described in other ways, and such instances are explained in the pertinent examples.

The substrate against which enzyme activity was measured was methyl 7-amino-3-methyl-3-cephem-4-carboxylate unless otherwise stated.

The substrate esters will spontaneously deesterify by hydrolysis in alkaline conditions. Thus, it is most important to avoid alkaline conditions when the activity of an enzyme preparation is being measured or to correct measured rates for the non-enzymatic hydrolysis rate.

Potassium hydrogen phosphate buffers were usually used in the examples below. These buffers are described as having certain pH's. The buffers were prepared by making solutions of potassium dihydrogen phosphate, and adjusting the pH to the desired point with potassium hydroxide or phosphoric acid.

The fermentation media were routinely steam-sterilized. Glucose and ammonium salts, when used, were added after sterilization as filter-sterilized aqueous solutions.

EXAMPLE 1

The enzyme was produced by inoculating a vegetative culture of *S. capillispira,* NRRL 12279, in 25 ml. of the following medium.

| Glucose | 25 g./liter |
|---|---|
| Corn starch | 10 |
| Liquid meat peptone | 10 |
| Enzymatically digested casein | 4 |
| Blackstrap molasses | 5 |
| $MgSO_4 \cdot 7H_2O$ | 0.5 |
| $CaCO_3$ | 2 |
| Czapek's minerals* | 2 ml./liter |
| *KCl | 100 g./liter |
| $MgSO_4 \cdot 7H_2O$ | 100 |
| $FeSO_4 \cdot 7H_2O$, dissolved in Conc. HCl | 2 |
| | 2 ml./liter |

The inoculated tube was shaken at 30° for 3 days, and then 4 ml. of the culture was transferred to a 50-ml. flask. To the flask was added 1 ml. of a filter-sterilized substrate solution containing 5 mg./ml. of methyl 7-amino-3-methyl-3-cephem-4-carboxylate at pH 7.0.

The flask was then incubated with shaking at 30° for 16–20 hours to allow the enzyme to deesterify the substrate compound.

At the end of the reaction time, the culture was centrifuged, and the pH was found to be 6.4. The supernatant from the centrifugation was evaluated by paper chromatography as described above, using 4/1 acetonitrile/water as the solvent. The chromatogram was acylated with a solution of phenoxyacetyl chloride in petroleum ether and overlaid on a plate of nutrient medium seeded with *B. subtilis,* and was found to produce a zone of inhibition. No zone of inhibition was produced by organisms which did not produce the deesterifying enzyme.

EXAMPLE 2

In this experiment the organism was grown in the same medium used in Example 1, in a 10-liter agitated tank supplied with air through a sub-surface sparger. The inoculant for the tank was prepared by inoculating one 250-ml. flask from slant culture of *S. capillispira,* and incubating the flask for 2 days at 30° with shaking. The medium in which the organism would be grown for enzyme production was prepared, supplemented with 3 ml. of a silicone antifoam, and the pH was adjusted to 6.7. The tank containing the medium was autoclaved for 1 hour at 121° (15 psi) to sterilize it. The tank and media were then cooled, the inoculum was added, and air flow and agitation were started. Air was sparged through the medium at about 5 standard liters/minute throughout the course of the fermentation, and the temperature was controlled at 30°. The fermentation was continued for 107 hours. The pH was periodically measured, and was found to increase as incubation continued. At 17 hours, and at 89, 99 and 101 hours, phosphoric acid was added to readjust the pH to 6.7.

Samples were taken from the tank at the beginning and end of each working day, and were frozen and evaluated as a group for enzyme activity. The samples were thawed, centrifuged, and mixed with the same substrate compound used in Example 1, and, after a 16-hour reaction period, were evaluated by paper chromatography. The highest deesterification activity was found in the sample taken from the fermentation at 67 hours. Activity was first found at 41 hours, and samples obtained after 67 hours tended to have less than maximum activity.

EXAMPLE 3

This experiment was carried out to evaluate a number of complex and defined media that would support growth of the microorganism and production of the deesterifying enzyme. The following media were used.

| A | | |
|---|---|---|
| Glucose | 15 g./liter | |
| Soybean grits | 15 | |
| Corn steep solids | 10 | |
| Tapioca dextrin | 20 | |
| $CaCO_3$ | 2 | |
| Czapek's minerals | 2 ml./liter | |
| Adjust pH to 6.8 | | |
| B | | |
| Glucose | 10 g./liter | |
| Molasses | 20 | |
| Peptone | 5 | |
| $CaCO_3$ | 2 | |
| Czapek's minerals | 2 ml. | |
| Adjust pH to 7.0 | | |
| C | | |
| Blackstrap molasses | 5 g./liter | |
| Distiller's solubles | 5 | |
| Soybean flour | 5 | |
| Peanut meal | 5 | |
| Pre-cooked oatmeal | 5 | |
| Glycerol | 10 | |
| Czapek's minerals | 2 ml./liter | |
| Adjust pH to 7.3 | | |
| D | | |
| Soybean grits | 15 g./liter | |
| Casein | 1.0 | |
| Glucose | 25 | |
| Blackstrap molasses | 3 | |
| $CaCO_3$ | 2.5 | |
| Czapek's minerals | 2 ml./liter | |
| Adjust pH to 7.4 | | |
| E | | |
| Glucose | 25 g./liter | |
| Corn starch | 10 | |
| Liquid meat peptone | 10 | |
| Enzymatically digested casein | 4 | |
| Blackstrap molasses | 5 | |
| $MgSO_4 \cdot 7H_2O$ | 0.5 | |
| $CaCO_3$ | 2 | |
| Czapek's minerals | 2 ml./liter | |
| F | | |
| Tryptone | 5 g./liter | |
| Yeast extract | 5 | |
| $K_2HPO_4$ | 5 | |
| Potato dextrin | 5 | |
| $MgSO_4 \cdot 7H_2O$ | 2 | |
| Glucose | 10 | |
| Czapek's minerals | 2 ml./liter | |
| Glycerol | 1 | |
| Adjust pH to 7.0 with $H_3PO_4$ | | |
| G | | |
| Raffinose | 2 g./liter | |
| Sucrose | 2 | |
| Galactose | 2 | |
| Soluble starch | 10 | |
| Pancreatic digest of casein USP | 5 | |
| $MgSO_4 \cdot 7H_2O$ | 0.5 | |
| $K_2HPO_4$ | 0.25 | |
| $(NH_4)_6Mo_7O_{24} \cdot 4H_2O$ | 0.1 | |
| Adjust pH to 7.0 | | |
| H | | |
| $(NH_4)_2HPO_4$ | 10 g./liter | |
| $Na_2SO_4$ | 0.5 | |
| $K_2HPO_4$ | 0.5 | |
| $MgSO_4 \cdot 7H_2O$ | 0.4 | |
| $FeSO_4 \cdot 7H_2O$ | 0.02 | |
| $MnSO_4 \cdot 4H_2O$ | 0.02 | |
| NaCl | 0.02 | |
| Yeast extract | 1 | |
| Glucose | 10 | |
| $H_3BO_3$ | 0.5 mg./liter | |
| $CuSO_4 \cdot 5H_2O$ | 0.04 | |
| $Na_2MoO_4 \cdot 2H_2O$ | 0.2 | |
| $ZnSO_4 \cdot 7H_2O$ | 8 | |
| $CaCl_2$ | 50 | |
| $CoCl_2 \cdot 6H_2O$ | 0.2 | |
| Adjust pH to 7.0 | | |
| I | | |
| Glutamic acid | 1 g./liter | |
| $MgSO_4 \cdot 7H_2O$ | 0.5 | |
| $K_2HPO_4$ | 2 | |
| $CaCO_3$ | 1 | |
| Glucose | 10 | |
| Czapek's minerals | 2 ml./liter | |
| Adjust pH to 7.0 with NaOH | | |
| J | | |
| Yeast extract | 2 g./liter | |
| $MgSO_4 \cdot 7H_2O$ | 0.5 | |
| $K_2HPO_4$ | 2 | |
| $CaCO_3$ | 1 | |
| Glucose | 10 | |
| Czapek's minerals | 2 ml./liter | |
| Adjust pH to 7.0 with $H_3PO_4$ | | |
| K | | |
| Sucrose | 20 g./liter | |
| Peptone | 5 | |
| $K_2HPO_4$ | 2 | |
| $MgSO_4 \cdot 7H_2O$ | 0.5 | |
| Czapek's minerals | 2 ml./liter | |
| Adjust pH to 7.0 with $H_3PO_4$ | | |

A 50 ml. portion of each of the above media was placed into a 250 ml. flask and autoclaved. After cooling each flask was inoculated from a vegetative culture of *S. capillispira* and incubated for 3 days at 30° with shaking. Then, a 4 ml. aliquot of each culture was mixed with 1 ml. of substrate stock, which was prepared by dissolving 5 mg./ml. of methyl 7-amino-3-methyl-3-cephem-4-carboxylate in 0.5-molar $KH_2PO_4$ buffer at pH 7.

The reaction mixtures were shaken at 30° for 16 hours, and were then evaluated by paper chromatography as described in Example 1.

It was found that the organism grew well in all of the above media. The chromatographic analysis showed that the deesterifying enzyme was produced in all of the media except medium H, which contains a number of heavy metal salts and a high level of $(NH_4)_2HPO_4$.

EXAMPLE 4

This example was carried out substantially according to the method of Example 3, to evaluate a number of other defined media, the formulae of which follow.

A

| | | |
|---|---|---|
| (NH$_4$)$_2$HPO$_4$ | 10 | g./liter |
| Na$_2$SO$_4$ | 0.5 | |
| K$_2$HPO$_4$ | 5 | |
| MgSO$_4$ . 7H$_2$O | 0.4 | |
| Yeast extract | 1 | |
| Glucose | 10 | |

Adjust pH to 7.0 with H$_3$PO$_4$

B

| | | |
|---|---|---|
| KH$_2$PO$_4$ | 10 | g./liter |
| Na$_2$SO$_4$ | 0.5 | |
| K$_2$HPO$_4$ | 5 | |
| MgSO$_4$ . 7H$_2$O | 0.4 | |
| Yeast extract | 1 | |
| Glucose | 10 | |

Adjust pH to 7.0 with KOH

C

| | | |
|---|---|---|
| (NH$_4$)$_2$HPO$_4$ | 10 | g./liter |
| Na$_2$SO$_4$ | 0.5 | |
| K$_2$HPO$_4$ | 5 | |
| MgSO$_4$ . 7H$_2$O | 0.4 | |
| FeSO$_4$ . 7H$_2$O | 0.02 | |
| MnSO$_4$ . 4H$_2$O | 0.02 | |
| NaCl | 0.02 | |
| Yeast extract | 1 | |
| Glucose | 10 | |

Adjust pH to 7.0 with H$_3$PO$_4$

D

| | | |
|---|---|---|
| (NH$_4$)$_2$HPO$_4$ | 10 | g./liter |
| Na$_2$SO$_4$ | 0.5 | |
| K$_2$HPO$_4$ | 5 | |
| MgSO$_4$ . 7H$_2$O | 0.4 | |
| CuSO$_4$ . 5H$_2$O | 0.04 | |
| Na$_2$MoO$_4$ . 2H$_2$O | 0.2 | |
| ZnSO$_4$ . 7H$_2$O | 8 | |
| CoCl$_2$ . 6H$_2$O | 0.2 | |
| Yeast extract | 1 | |
| Glucose | 10 | |
| H$_3$BO$_3$ | 0.5 | mg./liter |

Adjust pH to 7.0 with H$_3$PO$_4$

E

| | | |
|---|---|---|
| Glutamic acid | 5 | g./liter |
| MgSO$_4$ . 7H$_2$O | 0.5 | |
| K$_2$HPO$_4$ | 2 | |
| CaCO$_3$ | 1 | |
| Glucose | 10 | |
| Czapek's minerals | 2 | ml./liter |

Adjust pH to 7.0 with KOH

F

| | | |
|---|---|---|
| Glutamic acid | 5 | g./liter |
| MgSO$_4$ . 7H$_2$O | 0.5 | |
| K$_2$HPO$_4$ | 5 | |
| CaCO$_3$ | 1 | |
| Glucose | 10 | |
| Czapek's minerals | 2 | ml./liter |

Adjust pH to 7.0 with KOH

G

| | | |
|---|---|---|
| Yeast extract | 5 | g./liter |
| MgSO$_4$ . 7H$_2$O | 0.5 | |
| K$_2$HPO$_4$ | 2 | |
| CaCO$_3$ | 1 | |
| Glucose | 10 | |
| Czapek's minerals | 2 | ml/liter |

Adjust pH to 7.0 with H$_3$PO$_4$

H

| | | |
|---|---|---|
| Yeast extract | 5 | g./liter |
| MgSO$_4$ . 7H$_2$O | 0.5 | |
| K$_2$HPO$_4$ | 2 | |
| CaCO$_3$ | 1 | |
| Glucose | 10 | |
| Czapek's minerals | 2 | ml./liter |

The 250-ml. flasks containing 50 ml. each of media were sterilized, cooled, inoculated and incubated as described above in Example 3, and each culture was sampled and reacted with substrate compound according to the scheme of that example.

Analysis of the reaction mixtures by paper chromatography showed that the enzyme was not produced well in media A, C, D, E or F. The enzyme was produced, as evidenced by large zones of inhibition, in media B, G and H.

EXAMPLE 5

This experiment was carried out to evaluate the effect of a number of amino acids on the growth of the microorganism and production of the enzyme. A large amount of the following basal medium was prepared.

| | |
|---|---|
| MgSO$_4$ . 7H$_2$O | 0.5 g./liter |
| K$_2$HPO$_4$ | 2 |
| CaCO$_3$ | 1 |
| Czapek's minerals | 2 ml./liter |

The above medium was split into aliquots, and one amino acid was added to each aliquot to prepare test media, each of which contained 2 g./liter of the indicated amino acid.

(1) L-Glutamic acid
(2) L-Alanine
(3) L-Arginine
(4) L-Aspartic acid
(5) L-Glycine
(6) (L-Histidine HCl
(7) L-Proline
(8) L-Serine
(9) L-Threonine A 10 g./liter portion of sterile glucose was added to each medium, after sterilization.

The sterile media in 50 ml. portions contained in 250 ml. flasks were inoculated from vegetative cultures and incubated as described in the examples above. Each culture was sampled at 41 and 65 hours, and the activity of the de-esterifying enzyme was determined by the spot-plate method which was described above.

The table below reports the pH of each culture at the times of sampling, and the specific activity of the enzyme, which is defined as (moles × $10^{-10}$ ester hydrolyzed)/(mg. dry cells) (minute).

| | pH | | Specific Activity | |
|---|---|---|---|---|
| Medium | 41 Hr. | 65 Hr. | 41 Hr. | 65 Hr. |
| 1 | 7.5 | 7.3 | 3.7 | 3.2 |
| 2 | 7.4 | 6.1 | 1.8 | 3.2 |
| 3 | 6.8 | 6.7 | 3.1 | 1.6 |
| 4 | 7.9 | 7.1 | 3.4 | 4.7 |
| 5 | 7.3 | 6.8 | 4.3 | 3.8 |
| 6 | 7.4 | 6.6 | 2.2 | 10.2 |
| 7 | 6.8 | 6.6 | 5.0 | 0.8 |
| 8 | 7.2 | 6.6 | 5.0 | 5.7 |
| 9 | 6.8 | 6.5 | 8.2 | 5.7 |

EXAMPLE 6

Another experiment was carried out with a number of amino acids to determine the optimum medium for enzyme production. The basal medium in this experiment was as follows.

| | | |
|---|---|---|
| MgSO$_4$ . 7H$_2$O | 0.5 | g./liter |
| K$_2$HPO$_4$ | 2 | |
| CaCO$_3$ | 1 | |
| Glucose | 10 | |
| Czapek's minerals | 2 | ml./liter |

Aliquots of the basal medium were treated with 2 g./liter of the amino acids listed below.

The media were pH-adjusted to 7.0, sterilized, inoculated with a vegetative culture and incubated as described in the examples above. After 44 hours of incubation, 4-ml. samples of each culture were taken and mixed with 1 ml. each of a 5 mg./ml. solution of methyl 7-amino-3-methyl-3-cephem-4-carboxylate in 0.5-molar K$_2$HPO$_4$ buffer at pH 7.0. The substrate solution also contained 20 μg. of sodium azide per milliliter to stop growth of the cells. The reaction mixtures were agitated gently for 5 hours at 30°, and were assayed for esterase activity by the spot-plate method. The esterase activities are shown below.

| | Specific Activity |
|---|---|
| (1) Arginine | 24 |
| (2) Histidine | 5.1 |
| (3) Isoleucine | 9.0 |
| (4) Leucine | 10 |
| (5) Lysine | 9.0 |
| (6) Methionine | 13 |
| (7) Phenylalanine | 5.2 |
| (8) Threonine | 18 |
| (9) Tryptophan | 13 |
| (10) Valine | 7.5 |
| (11) Alanine | 4.4 |
| (12) Aspartic acid | 4.4 |
| (13) Cystine | 0 |
| (14) Glutamic acid | 6.7 |
| (15) Glycine | 22 |
| (16) Hydroxyproline | 11 |
| (17) Proline | 17 |
| (18) Serine | 24 |
| (19) Tyrosine | 13 |
| (20) Glutamine | 4.8 |
| (21) Asparagine | 7.1 |

EXAMPLE 7

This was another experiment carried out to evaluate the effect of various levels of amino acids in the culture medium. The basal medium was that used in Example 6. The basal medium was divided into aliquots and L-proline or L-serine was added to the aliquots in the concentrations shown in the table below. The media were dispensed, sterilized, cooled, inoculated and incubated as described above in Example 6, and were sampled after 48 hours and analyzed for esterase activity as described in that example. The results were as follows.

| Source | Concentration | Specific Activity |
|---|---|---|
| L-Proline | 2 g./liter | 9.7 |
| | 4 | 6.3 |
| | 6 | 3.1 |
| | 8 | 1.7 |
| | 10 | 1.5 |
| L-Serine | 2 | 14 |
| | 4 | 0 |
| | 6 | 5.7 |
| | 8 | 3.2 |

-continued

| Source | Concentration | Specific Activity |
|---|---|---|
| | 10 | 3.1 |

EXAMPLE 8

This experiment was carried out to evaluate the effect of varied amounts of ammonium ion in the fermentation medium. The basal medium used in this experiment was the same as that used in Example 6 above. Fifty-ml. portions of each medium were measured into 250-ml. flasks, and sterilized. Ammonium chloride was added from a filter sterilized stock solution after sterilization to provide amounts of ammonium ion from 0.05 g./liter to 0.6 g./liter. The flasks were inoculated with vegetative culture of S. capillispira and were incubated at 30° for 44 hours with constant shaking. Samples were then obtained from the flasks, the dry weight of cells per milliliter of culture was determined, and the esterase activity of the culture was measured as described in the example above, except that sodium azide was not used in the reaction medium.

The table below reports the dry weight of cells in each fermentation, in mg./ml., the specific activity, and the total activity, in (moles × 10$^{-7}$ ester hydrolyzed)/(liter of culture) (minute).

| NH$_4$$^+$ Conc. | Cell Dry Wt. (mg./ml.) | Specific Activity | Total Activity |
|---|---|---|---|
| 0.05 | 0.56 | 9.3 | 5.2 |
| 0.1 | 1.04 | 9.0 | 9.4 |
| 0.2 | 1.18 | 7.0 | 8.3 |
| 0.3 | 1.48 | 6.8 | 10.0 |
| 0.4 | 1.62 | 4.3 | 7.0 |
| 0.5 | 2.16 | 2.4 | 5.2 |
| 0.6 | 2.24 | 1.9 | 4.2 |

The results of this experiment show clearly the importance of providing sufficient nitrogen source to the fermentation, but not providing an excessive supply.

EXAMPLE 9

This experiment was carried out to evaluate the effect of trace metal ions on the growth of A49492 and enzyme production. Two basal media were used in this experiment.

| | I | II |
|---|---|---|
| L-Serine | 3.0 g./liter | 3.0 g./liter |
| MgSO$_4$ . 7H$_2$O | 0.5 | 0.5 |
| K$_2$HPO$_4$ | 2 | 2 |
| CaCO$_3$ | 1 | 1 |
| Glucose | 10 | 10 |
| Czapek's minerals | 2 ml./liter | — |

The media were pH-adjusted to 7.0 with phosphoric acid, and sterilized, and the glucose was added after sterilization.

Media were made up by using one of the above basal media, as shown in the table below, with added salts as shown below. The concentration of each salt is indicated in mg./liter. Flasks of each medium were filled, inoculated, and incubated for 48 hours as described in the example above, and samples were analyzed by the spot-plate technique, with the following results. Activity data are reported as described in Example 8 above.

-continued

| Medium | H$_3$BO$_3$, 1 mg./liter | CuSO$_4$ 0.08 | Na$_2$MoO$_4$ . 2H$_2$O, 0.4 | ZnSO$_4$ . 7H$_2$O, 16 | CoCl$_2$ . 6H$_2$O, 0.4 | MnSO$_4$ . H$_2$O, 0.4 | KCl, 200 | FeSO$_4$ . 7H$_2$O, 4 | MgSO$_4$ . 7H$_2$O, 200 | Cell Dry Wt. (mg/ml) | Specific Acitivity | Total Activity |
|---|---|---|---|---|---|---|---|---|---|---|---|---|
| I | x | x | x | x | x | x | | | | 3.66 | 1.4 | 5.1 |
| I | | x | | | | | | | | 1.88 | 1.8 | 3.4 |
| I | | | x | | | | | | | 2.22 | 2.2 | 4.9 |
| I | | | | x | | | | | | 2.56 | 2.0 | 5.1 |
| I | | | | | x | | | | | 3.62 | 3.2 | 11.6 |
| I | | | | | | x | | | | 1.96 | 3.2 | 6.3 |
| I | | | | | | | x | | | 2.2 | 2.0 | 4.4 |
| I | | | | | | | | | | 1.08 | 3.1 | 3.4 |
| II | | | | | | | x | | | 1.76 | 3.5 | 6.2 |
| II | | | | | | | | x | | 2.32 | 0.66 | 1.5 |
| II | | | | | | | | | x | 0.78 | 11 | 8.6 |

EXAMPLE 10

In this experiment, a number of different carbohydrates were added to the media to determine the effect of various carbon sources on production of the esterase. The following basal medium was used.

| | | |
|---|---|---|
| L-serine | 3 | g./liter |
| MgSO$_4$ . 7H$_2$O | 0.5 | |
| K$_2$HPO$_4$ | 2 | |
| CaCO$_3$ | 1 | |
| Czapek's minerals | 2 | ml./liter |
| Adjust pH to 7.0 with H$_3$PO$_4$ | | |

The carbohydrates used in the media, at 10 g./liter, are listed in the table below. The experiment was carried out as described in the experiments immediately above, and the results are reported as described in the examples immediately above.

| | Cell Dry Wt. (mg./ml.) | Specific Activity | Total Activity |
|---|---|---|---|
| D − Dextrose | 1.98 | 1.9 | 3.8 |
| Sucrose | 1.1 | 0 | 0 |
| Soluble starch | 1.72 | 2.0 | 3.4 |
| Potato dextrin | 2.3 | 2.5 | 5.8 |
| Glycerol | 2.08 | 2.1 | 4.4 |
| Fructose | 1.66 | 4.9 | 8.1 |
| D + Mannose | 0.64 | 5.8 | 3.7 |
| D + Lactose | 1.08 | <2.8 | <3.0 |
| Maltose | 0.66 | 23 | 15 |
| D − Ribose | 1.68 | 11 | 18.5 |
| D − Sorbitol | 0.62 | 5.0 | 3.1 |

EXAMPLE 11

In this experiment, the effect of a number of carbohydrates, including edible oils, was evaluated. Two basal media were used, as follows.

| Media I | | Media II | |
|---|---|---|---|
| L-Serine | 2 g./liter | L-Serine | 2 g./liter |
| MgSO$_4$ . 7H$_2$O | 0.5 | MgSO$_4$ . 7H$_2$O | 0.5 |
| K$_2$HPO$_4$ | 2 | K$_2$HPO$_4$ | 2 |
| CaCO$_3$ | 1 | CaCO$_3$ | 1 |
| | | ZnSO$_4$ . 7H$_2$O | 0.016 |
| | | KCl | 0.2 |
| | | CoCl$_2$ . 6H$_2$O | 0.004 |
| | | FeSO$_4$ . 7H$_2$O | 0.004 |
| Adjust pH to 7.0 with H$_3$PO$_4$ | | | |

To each portion of the basal media was added one of the sugars or oils indicated in the table below. Sugars were added at 10 g./liter, and oils were added at 3% by volume.

Media were stabilized, inoculated and incubated as described in the examples above. The incubation period was 48 hours. It was not possible to obtain accurate dry cell weights from those fermentations in which oils were used, because of the oily residue. Dry weights in those samples, accordingly, were estimated from the volume percent solids measured by centrifuging a sample of the oil-containing fermentation mixture.

The results of the experiment were as follows.

| Basal Medium | Carbohydrate | Cell Dry Wt. (mg./ml.) | Specific Activity | Total Activity |
|---|---|---|---|---|
| I | — | 0.48 | 0 | 0 |
| II | — | 0.33 | 0 | 0 |
| I | Glucose | 1.43 | 6.0 | 8.6 |
| II | Glucose | 1.85 | 4.9 | 9.1 |
| I | Ribose | 2.0 | 5.0 | 10.0 |
| II | Ribose | 2.42 | 2.0 | 4.8 |
| I | Maltose | 1.55 | 1.7 | 2.6 |
| II | Maltose | 1.35 | 1.8 | 2.4 |
| I | Cottonseed oil | 1.78 | 0 | 0 |
| II | Cottonseed oil | 4.15 | 1.2 | 5.0 |
| I | Corn oil | 1.78 | 1.2 | 2.1 |
| II | Corn oil | 1.78 | 0 | 0 |
| I | Soybean oil | 1.19 | 1.8 | 2.1 |
| II | Soybean oil | 2.96 | 2.0 | 5.9 |
| I | Peanut oil | 1.78 | 3.8 | 6.8 |
| II | Peanut oil | 3.56 | 1.7 | 6.1 |

EXAMPLE 12

A tank fermentation was carried out in a 5-liter agitated fermenter, equipped with a sub-surface air bubbler. The medium used was as follows.

| | | |
|---|---|---|
| NH$_4$Cl | 0.2 | g./liter |
| MgSO$_4$ . 7H$_2$O | 0.5 | |
| K$_2$HPO$_4$ | 2.0 | |
| CaCl$_2$ . 2H$_2$O | 0.2 | |
| ZnSO$_4$ . 7H$_2$O | 0.016 | |
| KCl | 0.2 | |
| CoCl$_2$ . 6H$_2$O | 0.0004 | |
| FeSO$_4$ . 7H$_2$O | 0.004 | |

| | |
|---|---|
| -continued | |
| Glucose | 10 |

The pH of the medium was adjusted to 7.0 with $H_3PO_4$ before sterilization, and the glucose and $NH_4Cl$ were added after sterilization from filter-sterilized stock solutions to desired concentrations.

Three liters of the above medium was added to the 5-liter fermenter, and an automatic pH controller was set up to control the pH at 6.95 by the addition of 0.5 N $NH_4OH$. Sterile air was supplied at 1.5–2 standard liters per minute, and a small amount of silicone anti-foam was added as needed to control foaming.

The fermentation was allowed to run for 93 hours, during which time 300 ml. of 20% glucose solution and 200 ml. of 0.5-molar $K_2HPO_4$ were added as needed at intervals. The temperature was automatically controlled at 30° C. throughout the fermentation.

Samples were taken at 22, 45, 69 and 93 hours, and were analyzed by the spot-plate method as described above using a 5-hour reaction period. The analytical results were as follows.

| | Cell Dry Wt. (mg./ml.) | Specific Activity | Total Activity |
|---|---|---|---|
| 22 hours | 0.73 | <4.6 | 3.4 |
| 45 | 1.79 | 5.0 | 9.0 |
| 69 | 4.23 | 4.8 | 20 |
| 93 | 5.72 | 4.7 | 27 |

EXAMPLE 13

A medium known as Spizizen's salts medium was used in this experiment. Its formula was as follows.

| | | |
|---|---|---|
| $K_2HPO_4$ | 14 | g./liter |
| $KH_2PO_4$ | 6 | |
| Sodium citrate | 1 | |
| $(NH_4)_2SO_4$ | 2 | |
| $MgSO_4 . 7H_2O$ | 0.2 | |
| $CaCO_3$ | 2 | |
| Glucose | 10 | |
| Salts solution* | 1 | ml./liter |
| *$FeSO_4 . 7H_2O$ | 100 | mg./liter |
| $MnCl_2 . 4H_2O$ | 100 | |
| $ZnSO_4 . 7H_2O$ | 100 | |

Flasks of the medium were prepared and sterilized, and the glucose was added as a filter-sterilized stock solution after sterilization. The flasks were inoculated with a vegetative culture, and were incubated with shaking at 30° for 48 hours, and analyzed as described in the examples above, by the spot-plate method, using a 5-hour reaction time. The dry weight of cells in the fermentation mixture was 3.26 mg./ml., and the specific activity was $6.8 \times 10^{-10}$ moles of ester hydrolyzed/(mg. dry cells) (minute), equivalent to $2.2 \times 10^{-6}$ moles of ester hydrolyzed/(liter of fermentation mixture) (minute).

EXAMPLE 14

This experiment was similar to the tank fermentation of Example 12, except that the medium contained 15 g./liter of glucose instead of 10 g./liter; the pH was controlled by addition of 1/1 $NH_4OH/NaOH$, both 0.5 N, to reduce the amount of ammonium ion being added; and the fermentation tank was inoculated with a spore suspension, obtained from a stored slant of S. capillispira, instead of from a vegetative culture.

In other respects, the fermentation was like that of Example 12, and was allowed to run for 71 hours. At the end of the fermentation, a sample was taken and analyzed by the spot-plate method, and was found to contain 4 mg./ml. of dry cells with a specific activity of $6.54 \times 10^{-10}$ moles of ester hydrolyzed/(minute) (mg. of dry cells), equivalent to $2.6 \times 10^{-6}$ moles of ester hydrolyzed/(minute) (liter of fermentation mixture).

EXAMPLE 15

A 10-liter fermentation was carried out, using the following medium.

| | |
|---|---|
| $NH_4Cl$ | 0.1 g./liter |
| $MgSO_4 . 7H_2O$ | 0.5 |
| $K_2HPO_4$ | 2 |
| $CaCl_2 . 2H_2O$ | 0.2 |
| $ZnSO_4 . 7H_2O$ | 0.16 |
| KCl | 2.0 |
| $CoCl_2 . 6H_2O$ | 0.004 |
| $FeSO_4 . 7H_2O$ | 0.04 |
| Glucose | 15 |

The pH of the medium was adjusted to 7.0 with phosphoric acid, and the glucose was added after steam sterilization of the tank and medium. The medium was inoculated with a vegetative culture of S. capillispira, and fermentation was started at 30°, with agitation and a sub-surface air flow of 2.5 standard liters/minute of sterile air. The pH of the fermentation mixture was controlled at 7.0 by the automatic addition of 2 N ammonium hydroxide.

At 67 hours, the air flow was changed to 5 standard liters/minute, in an attempt to strip off excess ammonia. Six ml. of silicone antifoam was necessary to keep down excessive foaming.

The fermentation mixture was sampled and analyzed at 91.5 hours, and was found to contain 3.28 mg./ml. of dry cells, with a specific activity of $7.48 \times 10^{-10}$ moles of ester hydrolyzed/(minute) (mg. of dry cells), equivalent to $2.5 \times 10^{-6}$ moles of ester hydrolyzed/(minute) (liter of fermentation mixture). The tank was harvested at 97 hours, and filtered to obtain 510 g. of wet cells.

An 8 g. sample of the wet cells was diluted to 20 ml. with 2 mM $K_2HPO_4$ at pH 8.0, homogenized, disrupted by sonication, and centrifuged to obtain a supernatant which contained 14.4 mg./ml. of protein by the ultraviolet analytical method of Warburg and Christian, Biochem. Z. 310, 384–421 (1942), and had an activity, measured against methyl 7-amino-3-methyl-3-cephem-4-carboxylate, of $2.2 \times 10^{-5}$ moles of ester hydrolyzed/(minute) (liter).

A 120 g. portion of the wet cells was diluted to 240 ml. with 2 mM $K_2HPO_4$ at pH 8.0, and homogenized with a hand-operated piston homogenizer. The homogenate was then disrupted by sonication with a probe-type ultrasound generator, using seven 30-second bursts of ultrasonic energy, and the sonicate was centrifuged for 30 minutes at 0° under 36,000 G. The supernatant from the centrifugation amounted to 200 ml., and was lyophilized to obtain 3.76 g. of dry enzyme preparation.

One g. of the lyophilized powder was suspended in 15 ml. of 2 mM $K_2HPO_4$ at pH 8.0, and was centrifuged under the same conditions as above. The supernatant, about 14 ml., was chromatographed on a 2.5 cm. × 8 cm.

column of cross-linked allyl dextran-methylene bisacrylamide (Sephacryl, Pharmacia Fine Chemicals, Piscataway, N.J. The column was eluted with the same buffer used to suspend the lyophilized powder, and fractions of approximately 5 ml. were collected. Esterase activity was found in the fractions from 200 ml. to 250 ml. of eluted liquid. Protein contents of the esterase-containing fractions ranged from 0.42 mg./ml. to 1.13 mg./ml., and esterase activities of the active fractions ranged from $1.1 \times 10^{-4}$ to $1.9 \times 10^{-6}$ moles of ester hydrolyzed/(minute) (liter).

EXAMPLE 16

A 34 g. portion of washed wet cells, which had been filtered from the fermentation mixture, washed with $K_2HPO_4$ buffer and frozen, were thawed and diluted to 170 ml. with 1 mM $K_2HPO_4$ buffer containing 1.5 mM dithiothreitol at pH 7.0. The suspension was homogenized through a hand-operated piston homogenizer, and the homogenate was centrifuged at 0° for 20 minutes under 36,000 G. The supernatant, 140 ml., was analyzed for protein and found to contain 8.1 mg./ml., and to have an activity, measured by the spot-plate method, of $1.9 \times 10^{-5}$ moles of ester hydrolyzed/(minute) (liter).

The enzyme solution was further purified by precipitation with ammonium sulfate, by adding 31.2 g. of ammonium sulfate to it, stirring to dissolve, and centrifuging for 20 minutes at 0° under 36,000 G. The pellet from the centrifugation was discarded, and to the supernatant was added an additional 30.6 g. of ammonium sulfate, and the suspension was centrifuged as above.

The pellet from the second centrifugation was dissolved in 30 ml. of the same buffer used above, and the solution was dialyzed against two 4-liter changes of 1 mM $K_2HPO_4$ at pH 7.2. The solution was found to contain 7.5 mg./ml. of protein. It was further dialyzed, resulting in a solution having a volume of 65 ml., which was stored by freezing.

A substrate solution containing about 2 mg./ml. of methyl 7-amino(phenyl)acetamido-3-methyl-3-cephem-4-carboxylate (methyl cephalexin) was prepared in water, at pH 7.2. A 1.25 ml. portion of this solution was combined with 3 ml. of the purified enzyme solution above and 0.75 ml. of 0.5 M $K_2HPO_4$ buffer, to prepare a solution having a protein concentration of 4.5 mg./ml., at pH 7.2. The mixture was shaken at 30° for 4 hours, and was then analyzed by paper chromatography, overlaying the chromatograms on nutrient agar plates seeded with *Sarcina lutea*. Large zones of inhibition were visible on the plate, indicating that the cephalexin ester was deesterified to yield the antibiotic cephalexin.

EXAMPLE 17

In this experiment, the enzyme preparation of Example 16 was used to deesterify methyl cephalexin, and the rate of hydrolysis was measured by pH-stat titration. Reaction mixtures were prepared as shown in Example 16, except that 1 ml. of the enzyme preparation and 2 ml. of substrate solution were used, so that the final reaction mixture contained 2.5 mg./ml. of protein.

Reactions were performed at pH 7 and pH 8. At pH 7, the rate of deesterification was found to be $4.0 \times 10^{-6}$ moles/(minute) (liter) of reaction mixture, and at pH 8, the rate was $1.36 \times 10^{-5}$ moles/(minute) (liter).

EXAMPLE 18

A purified enzyme preparation, prepared substantially as described in Example 15 above, and containing 0.66 mg./ml. of protein was used to deesterify methyl 7-amino(phenyl)acetamido-3-chloro-3-cephem-4-carboxylate(methyl cefaclor). The reaction mixture was made up of 0.5 ml. of the enzyme preparation, 1.25 ml. of water, and 0.25 ml. of 10 mg./ml. methyl cefaclor solution. The reaction was run for 10 minutes at pH 8 and 24°. As measured by pH-stat titration, the rate was found to be $5.8 \times 10^{-5}$ moles of ester hydrolyzed/(minute) (liter) of reaction mixture.

EXAMPLE 19

An enzyme preparation containing 1.27 mg./ml. of protein, purified over a Sephacryl column as described in Example 15, was used to determine the rates of deesterification of methyl 7-amino-3-methyl-3-cephem-4-carboxylate by the enzyme at various temperatures from 15° to 35°. Reaction mixtures were made up containing 0.4 ml. of the enzyme solution, 0.6 ml. of water and 1 ml. of 20 mg./ml. substrate solution. The pH of the reaction mixtures was 8.0.

Reactions were run on the automatic titrator, making appropriate corrections for the hydrolysis rates in the absence of the enzyme, and the highest reaction rate was found to be at 30°, $1.9 \times 10^{-5}$ moles of ester hydrolyzed/(minute) (liter of reaction mixture). The lowest reaction rate was at 15°, $1.0 \times 10^{-5}$ moles/(minute) (liter). At 35°, the enzyme was found to be unstable and no meaningful deesterification rates could be measured.

EXAMPLE 20

The following experiment was carried out to evaluate the possibility of immobilizing the esterase of this invention. An enzyme solution was prepared by Sephacryl purification substantially as described in Example 15, and was found to contain 0.75 mg./ml. of protein with activity of $3.5 \times 10^{-4}$ moles of ester hydrolyzed/(minute) (liter). A 30 ml. portion of the preparation was ultrafiltered using an Amicon (Lexington, Mass.) PM 30 membrane with 8 psig. of nitrogen pressure on the enzyme side. As ultrafiltration proceeded, additional portions of water were added as necessary until a total of 315 ml. of liquid was collected. The final volume of the dialyzed enzyme preparation was 30 ml., containing 0.34 mg./ml. of protein, with an activity of $7.2 \times 10^{-5}$ moles of ester hydrolyzed/(minute) (liter).

The following enzyme supports were used to immobilize the enzyme.

(1) DEAE-Sephadex (diethylaminoethyl weakly basic ion exchange resin, Pharmacia Fine Chemicals)

(2) DEAE-Sephacel (diethylaminoethyl cellulose bead ion exchange resin, Pharmacia Fine Chemicals)

(3) DEAE-Cellulose, Sigma Chemical Co., St. Louis, Mo.

(4) Cellex-CM, Bio-Rad Laboratories, Richmond, Cal.

(5) Bentonite (6) DEAE-Cellulose beads, prepared as described by Tsao and Chen, U.S. Pat. No. 4,063,017

A 1.5 mg. portion (dry weight) of each of the above supports was washed with pH 8 $K_2HPO_4$ buffer and then with water, and was mixed with 3.53 ml. of the enzyme preparation, the pH of which was adjusted to 8.0 before combining with the support. The mixtures were gently stirred for 18 hours at 4°.

Each of the support-enzyme systems was washed with pH 7.0 K₂HPO₄ buffer to remove any enzyme which was not immobilized on the support, and the wash liquids and the washed supported enzymes were reacted with methyl 7-amino-3-methyl-4-carboxylate to determine the amount of enzyme which was immobilized on the support. The analyses indicated the following portions of the enzyme activity to be immobilized.
(1) 24%
(2) 33%
(3) 34%
(4) 8%
(5) 6%
(6) 40%

The immobilized enzyme preparations were held at 40°, and were frequently analyzed to determine the half-life of the enzyme. The following results were found.

| Unsupported enzyme | 5 minutes |
|---|---|
| (1) | 4 minutes |
| (2) | 3.5 minutes |
| (3) | 5.5 minutes |
| (4) | unmeasurable due to low activity |
| (5) | unmeasurable due to low activity |
| (6) | 13 minutes |

We claim:

1. A process for deesterifying cephalosporin methyl esters of the formula

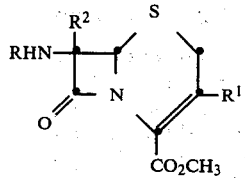

wherein
R is hydrogen or $R^3CH(NH_2)CO-$; $R^1$ is methyl, chloro, acetoxymethyl, methoxy, methoxymethyl, aminocarbonyloxymethyl, methylthiadiazolylthiomethyl or methyltetrazolylthiomethyl;
$R^2$ is hydrogen or methoxy;
$R^3$ is phenyl, cyclohexadienyl, cyclohexadienyl monosubstituted with hydroxy, or phenyl mono- or disubstituted with halo, hydroxy, $C_1-C_3$ alkyl or $C_1-C_3$ alkoxy; which process comprises contacting the methyl ester with the enzyme produced by culturing Streptomyces capillispira under enzyme-producing conditions.

2. A process of claim 1 for deesterifying a methyl ester wherein $R^1$ is methyl or chloro.

3. A process for claim 1 for deesterifying a methyl ester wherein $R^2$ is hydrogen.

4. A process of claim 1 for deesterifying a methyl ester wherein R is hydrogen.

5. A process of claim 1 for deesterifying a methyl ester wherein R is $R^3CH(NH_2)CO-$, and $R^3$ is phenyl.

6. A process of claim 2 for deesterifying a methyl ester wherein $R^2$ is hydrogen.

7. A process of claim 6 for deesterifying a methyl ester wherein R is hydrogen.

8. A process of claim 6 for deesterifying a methyl ester wherein R is $R^3CH(NH_2)CO-$, and $R^3$ is phenyl.

9. A process of any of claims 1-8 wherein the temperature is from about 15° to about 45°.

10. A process of claim 9 wherein the pH is from about 7 to about 9.

11. A process of claim 10 wherein the temperature is from about 25° to about 30°.

12. A process of claim 11 wherein the concentration of the methyl ester is from about 1 to about 10 mg./ml.

13. The enzyme which is produced by Streptomyces capillispira when cultured under enzyme-producing conditions, which enzyme deesterifies methyl esters of cephalosporin compounds of the formula

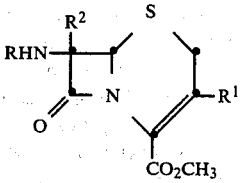

wherein
R is hydrogen or $R^3CH(NH_2)CO-$; $R^1$ is methyl, chloro, acetoxymethyl, methoxy, methoxymethyl, aminocarbonyloxymethyl, methylthiadiazolylthiomethyl or methyltetrazolylthiomethyl;
$R^2$ is hydrogen or methoxy;
$R^3$ is phenyl, cyclohexadienyl, cyclohexadienyl monosubstituted with hydroxy, or phenyl mono- or disubstituted with halo, hydroxy, $C_1-C_3$ alkyl or $C_1-C_3$ alkoxy.

14. A process for preparing an enzyme which deesterifies cephalosporin methyl esters of the formula

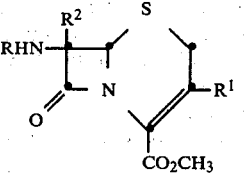

wherein
R is hydrogen or $R^3CH(NH_2)CO-$; $R^1$ is methyl, chloro, acetoxymethyl, methoxy, methoxymethyl, aminocarbonyloxymethyl, methylthiadiazolylthiomethyl or methyltetrazolylthiomethyl;
$R^2$ is hydrogen or methoxy;
$R^3$ is phenyl, cyclohexadienyl, cyclohexadienyl monosubstituted with hydroxy, or phenyl mono- or disubstituted with halo, hydroxy, $C_1-C_3$ alkyl or $C_1-C_3$ alkoxy; which process comprises culturing the microorganism Streptomyces capillispira under enzyme-producing conditions.

15. A process of claim 14 wherein the culture is carried out in a defined medium.

16. A process of claim 15 wherein the culture is carried out at a temperature from about 25° to about 40°.

17. A process of claim 16 wherein the culture is carried out at from about 30° to about 37°.

18. A process of claim 17 wherein the culture is carried out at a pH from about 6 to about 8.

19. A process of claim 18 wherein the medium contains ammonium ions.

20. A process of claim 19 wherein the pH of the culture medium is maintained at from about 6.5 to about 7.5 by the controlled addition of ammonium hydroxide.

* * * * *